US010155121B2

United States Patent
Zao et al.

(10) Patent No.: US 10,155,121 B2
(45) Date of Patent: Dec. 18, 2018

(54) STIMULI GENERATING METHODS, DEVICES AND CONTROL SYSTEMS TO INDUCE VISUAL EVOKED POTENTIALS USING IMPERCEPTIBLE FLICKERING MULTI-COLOR LIGHTS

(71) Applicant: National Chiao Tung University, Hsinchu (TW)

(72) Inventors: John Kar-Kin Zao, Hsinchu (TW); Yi-Pai Huang, Hsinchu (TW); Tzyy-Ping Jung, Hsinchu (TW); Fang-Cheng Lin, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 638 days.

(21) Appl. No.: 13/974,080

(22) Filed: Aug. 23, 2013

(65) Prior Publication Data

US 2014/0058483 A1 Feb. 27, 2014

Related U.S. Application Data

(60) Provisional application No. 61/693,269, filed on Aug. 25, 2012.

(51) Int. Cl.
*A61B 5/0484* (2006.01)
*A61N 5/06* (2006.01)

(52) U.S. Cl.
CPC ............ *A61N 5/06* (2013.01); *A61B 5/04842* (2013.01); *A61N 5/0622* (2013.01); *A61N 2005/0652* (2013.01); *A61N 2005/0663* (2013.01)

(58) Field of Classification Search
CPC ... A61B 5/0476; A61B 5/0482; A61B 5/0484; A61B 5/04842
See application file for complete search history.

(56) References Cited

U.S. PATENT DOCUMENTS 5,403,261 A * 4/1995 Shimizu ............... A61M 21/00
600/27
7,123,955 B1 10/2006 Gao et al.
(Continued)

FOREIGN PATENT DOCUMENTS

CN 1248426 3/2000
CN 1420745 5/2003
(Continued)

OTHER PUBLICATIONS

Wang et al., "A Cell-Phone-Based Brain-Computer Interface for Communication in Daily Life," Journal of Neural Engineering, Mar. 24, 2011, 025018, vol. 8.
(Continued)

*Primary Examiner* — Niketa Patel
*Assistant Examiner* — Nathan A Baldwin
(74) *Attorney, Agent, or Firm* — Knobbe Martens Olson & Bear LLP

(57) ABSTRACT

Visual or photic stimuli generating methods, devices and control systems for inducing steady-state visual evoked potential (SSVEP) from human viewers without causing discomfort to the viewers or distorting the embedding images are disclosed. The control system includes a stimuli-generating device and an electroencephalography (EEG) sensing device. The stimuli-generating device includes a first and a second light source. The first light source generates a flickering light with a first wavelength while a second light source generates another flickering light with one or more wavelength(s) differ from that of the first one. Together, the light sources generate visual/photic stimuli flickering above their critical flicker fusion threshold while maintaining the colorfulness and hue of the embedding images. At least one electrode of the EEG sensing device is connected to each viewer, configured to receive and analyze (Continued)

his/her EEG signals in order to detect and determine his/her responses to the stimuli.

16 Claims, 8 Drawing Sheets

(56) References Cited

U.S. PATENT DOCUMENTS

| | | | | |
|---|---|---|---|---|
| 2005/0088617 | A1* | 4/2005 | Hsieh | G06F 3/015 351/205 |
| 2010/0130812 | A1* | 5/2010 | Martel | A61M 21/02 600/27 |
| 2013/0053929 | A1* | 2/2013 | Colbaugh | A61M 21/02 607/90 |
| 2013/0266325 | A1* | 10/2013 | Giustiniano | H04B 10/116 398/130 |

FOREIGN PATENT DOCUMENTS

| | | |
|---|---|---|
| CN | 1776572 | 5/2006 |
| CN | 2888524 | 4/2007 |
| TW | 200945042 | 11/2009 |
| WO | 2012044261 | 4/2012 |

OTHER PUBLICATIONS

Middendorf et al., "Brain-Computer Interfaces Based on the Steady-State Visual-Evoked Response," IEEE Transactions on Rehabilitation Engineering, Jun. 2000, vol. 8, No. 2, p. 211-214.

Kluge et al., "Phase Coherent Detection of Steady-State Evoked Potentials: Experimental Results and Application to Brain-Computer Interfaces," Proceedings of the 3rd International IEEE EMBS Conference on Neural Engineering Kohala Coast, Hawaii, USA, May 2-5, 2007, p. 425-429.

Resalat et al., "Real-time Monitoring of Military Sentinel Sleepiness Using a Novel SSVEP-Based BCI System," 2012 IEEE EMBS International Conference on Biomedical Engineering and Sciences Langkawi Dec. 17-19, 2012, p. 740-745.

Lalor et al., "Steady-State VEP-Based Brain-Computer Interface Control in an Immersive 3D Gaming Environment," EURASIP Journal on Applied Signal Processing Jan. 1, 2005 :19, 3156-3164.

* cited by examiner

STIMULI GENERATING METHODS, DEVICES AND CONTROL SYSTEMS TO INDUCE VISUAL EVOKED POTENTIALS USING IMPERCEPTIBLE FLICKERING MULTI-COLOR LIGHTS

CROSS-REFERENCE TO RELATED APPLICATION

This application claims the priority benefit of U.S. application Ser. No. 61/693,269, filed on Aug. 25, 2012. The entirety of the above-mentioned patent application is hereby incorporated by reference herein and made a part of this specification.

BACKGROUND

Field of the Invention

The present invention is related to a control technique and a stimuli generating technique in connection with visual evoked responses. More particularly, the present invention is related to stimuli generating methods, devices and control systems for inducing visual evoked potentials from human viewers using imperceptible flickering multi-color lights.

Description of Related Art

In recent years, with the progress of medical engineering, brain computer interface (BCI) based on steady-state visual evoked potential (SSVEP) responses are widely applied. By the "steady-state visual evoked potential (SSVEP)" technique, the visual nerves of a human viewer's brain are stimulated with signals continuously flickering at a fixed frequency so as to induce the brain to generate electroencephalographic (EEG) signals corresponding to the flickering signals at the frequency. The generated EEG signals are referred to as steady-state visual evoked potential (SSVEP) signals, which may also be referred to as visual evoked responses. For the conventional technologies, the SSVEP signals are more reliable than the other types of visual evoked potential (VEP) and have a higher information transfer rate (ITR). Thus, the SSVEP technique has become a technique with quite considerable potential for development and can be applied to disability aids fields (including the driving of wheel chairs or for the dialing of mobile phones).

However, in the technique, the flickering signals used to induce the EEG signals generally employ flickering light sources with a mono wavelength and at a lower frequency (e.g., lower than 15 Hz) as stimuli sources for the human viewer's brain. The reason is that the frequency of the flickering light sources is inversely proportional to signal intensity of the SSVEP signals. That is to say, when the flickering light sources are at a lower frequency, signal intensity of the SSVEP signals will be stronger as to be detected easily. Nevertheless, when the frequency of the flickering light sources become further lower, visual fatigue or discomfort may be caused to the viewer due to the flickering lights, and even worse, diseases, such as migraine and seizure attacks of epilepsy, may be caused to the viewer. Therefore, if the technique has to be extended to the application in everyday life for ordinary people, it may be difficulty acceptable for the market due the aforementioned reasons.

Moreover, the flickering signals to induce the EEG signals typically use mono-color and simple patterns, such as checkerboard grid patterns or block graphic patterns, as visual stimuli patterns for the viewer. Therefore, the patterns provided by the conventional techniques can not be combined to display videos and images viewed by the ordinary viewers and thus, have difficult to encode the visual stimuli patterns into display images. Further, the visual stimuli patterns have lower flickering frequencies, which leads to distortion of encoded images and have to be calibrated with additional digital image processing techniques.

SUMMARY

The present invention is directed to stimuli generating methods, devices and control systems to alter a viewer's brain state and/or induce measurable responses of the viewer's neural cortices using imperceptible flickering multi-color lights, in which a stimulating light source (for example the first light thereof) consisting of one or more color lights each with distinct radiation spectrum, specific flickering frequency, amplitude, phase, spatial luminance/brightness distribution, and temporal waveform is combined with a compensating light source (for example the second light thereof) consisting also of one or more color lights each with distinct radiation spectrum, specific or randomized flickering frequency, amplitude, phase, spatial luminance/brightness distribution, and temporal waveform, and are applied as the visual stimuli to the opened eyes or the photic stimuli to the closed eyes of human viewer(s) who receive the lights. During the stimulation process, the combination of the stimulating light and the compensating light—which is referred collectively as the imperceptible stimuli thereof—flicker near or above the critical fusion frequency (CFF) threshold of the composite color light in human vision. Thus, the viewer(s) of the imperceptible stimuli perceive minimal or no flickering/flashing of the composite light and have significantly reduced risks of experiencing any discomfort or pathological side effects such as migraine or seizure attacks. Thereby, a brain-computer interfacing (BCI) technique that is safe, comfortable and capable of real-time brain state monitoring and/or alteration can be provided.

The responses of viewer's neural cortices can be observed or measured using electroencephalography (EEG), especially in the forms of visual evoked potentials (VEP) or steady-state visual evoked potentials (SSVEP), magnetoencephalography (MEG), functional near-infrared spectroscopy (fNIRS), functional magnetic resonance imaging (fMRI) or other neural imaging techniques.

The alterations of viewer's brain state can manifest as the changes in the activity levels of neuronal circuits and neural cortices as well as the changes in the complexity and spatial coherency and temporal synchronicity of neural activities. These alterations may result in improvements in viewer's physiological or psychological conditions for examples: the reduction of anxiety, depression, migraine severity or a pause of seizure.

The present invention provides a stimuli-generating device. The stimuli-generating device includes a first (stimulating) light source and a second (compensating) light source. The first light source comprises one or more color light(s), each of which has a specific wavelength, a specific spatial luminance distribution and a specific temporal waveform along with a specific flickering frequency, amplitude and/or phase to serve the purpose of inducing specific neural responses and/or causing specific changes of brain states of the viewer(s). The second light source also comprises one or more color light(s) with specific or randomized flickering frequency, amplitude, phase, spatial luminance distributions and temporal waveforms. The combined effects of the first (stimulating) light and the second (compensating) light minimizes viewers' flickering sensation towards the composite light and preserves the hue and the colorfulness of the displayed images produced by these light sources.

The pulse width or duty cycle of the first (stimulating) light is less than the pulse width or duty cycle of the second (compensating) light, the highest amplitude of the first light is greater than the highest amplitude of the second light, and the power generated by the first light and the power generated by the second light during each refresh cycle of the displayed images is equal to a proper ratio determined by the hue and the colorfulness of the displayed images.

In an embodiment of the present invention, the waveforms of the light pulses generated by the first (stimulating) light source and/or the second (compensating) light source are smoothened to those of the tapering functions such as Hanning or Blackman windows so that the power of these light pulses is concentrated in a narrow range of frequencies.

In an embodiment of the present invention, the flickering frequency of the combination of the first (stimulating) light and the second (compensating) light is equal to or higher than the critical fusion frequency (CFF) threshold of the composite color light in human vision. Specifically, the flickering frequency of the first (stimulating) light is within a range from 20 Hz to 65 Hz.

In an embodiment of the present invention, the first (stimulating) light source and the second (compensating) light source are disposed on different light-emitting positions.

In an embodiment of the present invention, the pulses from the first (stimulating) light and those from the second (compensating) light source are offset with specific time delays or asynchronous with variable time delays from one another.

In an embodiment of the present invention, the stimuli-generating device is an image display apparatus, a lighting apparatus or a light source indication apparatus.

According to another aspect, the present invention provides a control system to induce visual evoked potentials using imperceptibly flickering multi-color lights. The control system includes a stimuli-generating device and an EEG sensing device. The stimuli-generating device includes a first (stimulating) light source and a second (compensating) light source. The first light source is configured to generate one or more color light(s), each of which has a specific wavelength, a special spatial luminance distribution and a specific temporal waveform along with specific flickering frequency, amplitude and phase to serve the purpose of inducing specific neural responses and/or causing specific changes of brain states of the human viewers. The second light source is configured to generate one or more color light(s) with specific or randomized spatial luminance distributions and temporal waveforms to serve the purpose of compensating the stimulating light in order to minimize viewer's flickering sensation and to preserve the hue, the colorfulness and the general display effects of the color image. The flickering frequency of the combination of the first light and the second light is equal to or higher than the critical fusion frequency (CFF) threshold of the composite color light in human vision. The pulse width or duty cycle of the first light is less than the pulse width or duty cycle of the second light, the highest amplitude of the first light is greater than the highest amplitude of the second light, and the power generated by the first light and the power generated by the second light during each refresh cycle of the displayed images is equal to a proper ratio determined by the hue and the colorfulness of the displayed images.

At least one electrode of the EEG sensing device is connected to a viewer's head. When the viewer is stimulated by the first (stimulating) light and the second (compensating) light, the EEG sensing device is configured to receive an EEG signal of the viewer through the at least one electrode and analyze the EEG signal.

In an embodiment of the present invention, the EEG sensing device includes an EEG signal amplifier, a signal processor, a symbol detector and an event indicator. The EEG signal amplifier is coupled to the at least one electrode and configured to amplify an EEG signal of a viewer through the at least one electrode when the viewer is simulated by the combination of the first (stimulating) light and the second (compensating) light. The signal processor is coupled to the EEG signal amplifier and configured to reduce noise in the EEG signal. The symbol detector is coupled to the signal processor and configured to decode the EEG signal according to the frequency of the first (stimulating) light source and the frequency of the second (compensating) light source to generate a decoded signal. The event indicator is coupled to the symbol detector and configured to receive the decoded signal and generate an analysis result of the viewer's brain according to the decoded signal.

In an embodiment of the present invention, the stimuli-generating device further includes a light stimuli encoder. The light stimuli encoder coupled to the first light (stimulating) source and the second (compensating) light source and respectively modulates the flickering frequency, the amplitude and the pulse widths (duty cycles) of each of the first light and the second light, such that the power generated by the first light and the second light during each refresh cycle of the displayed images is equal to a proper ratio determined by the hue and the colorfulness of the displayed images.

According to still another aspect, the present invention provides a stimuli generating method to induce visual evoked potentials using imperceptibly flickering multi-color lights. The method includes the following steps. A first (stimulating) light consisting of one or more color light(s), each of which has a specific wavelength, a specific spatial luminance distribution and a specific temporal waveform along with a specific flickering frequency, amplitude and/or phase is generated. A second (compensating) light consisting also of one or more color lights each with distinct radiation spectrum, specific or randomized flickering frequency, amplitude, phase spatial luminance/brightness distribution, and temporal waveform is generated. The pulse width or duty cycle of the first light is less than the pulse width or duty cycle of the second light, the highest amplitude of the first light is greater than the highest amplitude of the second light, and the power generated by the first light and the second light during each refresh cycle of the displayed images is equal to a proper ratio determined by the hue and the colorfulness of the displayed images. When a viewer is stimulated by combination of the first (stimulating) light and the second (stimulating) light, an EEG signal of the viewer is received through at least one electrode, and the EEG signal is analyzed.

The stimuli-generating methods, devices and control systems described in this disclosure may be implemented within or by one or more of a general purpose microprocessor, digital signal processor (DSP), application specific integrated circuit (ASIC), field programmable gate array (FPGA), programmable logic devices (PLDs), or other equivalent logic devices. Accordingly, the terms "processor" or "controller," as used herein, may refer to any one or more of the foregoing structures or any other structure suitable for implementation of the techniques described herein.

The control system proposed in the embodiments of the present invention may be further combined with image transmission technology for achieving applications in fields for the viewer, such as visual tracking, visual manipulation, brain medical testing, industrial safety, human-computer interaction interface and so on.

Based on the aforementioned control system, methods, and devices for generating the imperceptible flickering multi-color visual/photic stimuli, the viewer's brains are evoked to produce measurable responses and/or alter their states by the combination of stimulating and compensating lights. The combination of stimulating and compensating lights can be generated by various types of display apparatuses and illumination systems. As a result, these imperceptible stimuli can be embedded into illuminating lights, still images, moving pictures.

In order to make the aforementioned and other features and advantages of the present invention more comprehensible, several embodiments accompanied with figures are described in detail below.

BRIEF DESCRIPTION OF THE DRAWINGS

The accompanying drawings are included to provide a further understanding of the present invention, and are incorporated in and constitute a part of this specification. The drawings illustrate embodiments of the present invention and, together with the description, serve to explain the principles of the present invention.

DESCRIPTION OF EMBODIMENTS

In order to establish stimuli-generating methods, devices and control systems to induce steady-state visual evoked potential (SSVEP) using imperceptibly-flickering stimuli lights, in the embodiments of the present invention, two or more lights having different wavelengths are employed for encoding, and a distribution of spectrums and energies (i.e., brightness) of the lights is adaptively modulated, such that the combination of the two or more lights may be hidden in a video, an image or illumination lights of a display, and the generation of electroencephalographic (EEG) signals may be easily perceived by a SSVEP stimuli system. Specifically, a stimuli light generated according to one or more embodiments of the present invention is combined by two or more lights having different wavelengths, which cause minimal or no flickering perception to the viewers of the combined lights. Besides, the stimuli lights embedded into images will not distort the color images. Moreover, the stimuli-generating device (also referred as to a light generating device) provided by the present invention may enhance perception efficiency of EEG signals through spatial frequency modulation and pulse modulation between each of the lights with different wavelengths as well as reduce discomfort caused to human eyes by the flickering lights. On the other hand, when the stimuli lights with high energies are emitted to the viewer with his/eyes closed, the viewer's brain may be directly stimulated by the stimuli lights due to a light-transmission effect, and SSVEP responses are accordingly produced from the viewer's brain. Several examples will be illustrated as references in the embodiments of the present invention and each technical detail of the embodiment of the present invention will also be described below. However, the spirit of the embodiments of the present invention is not limited to the illustrated examples below, and technical modifications and extensions may be properly made through applications of the embodiments of the present invention.

Figure 1:
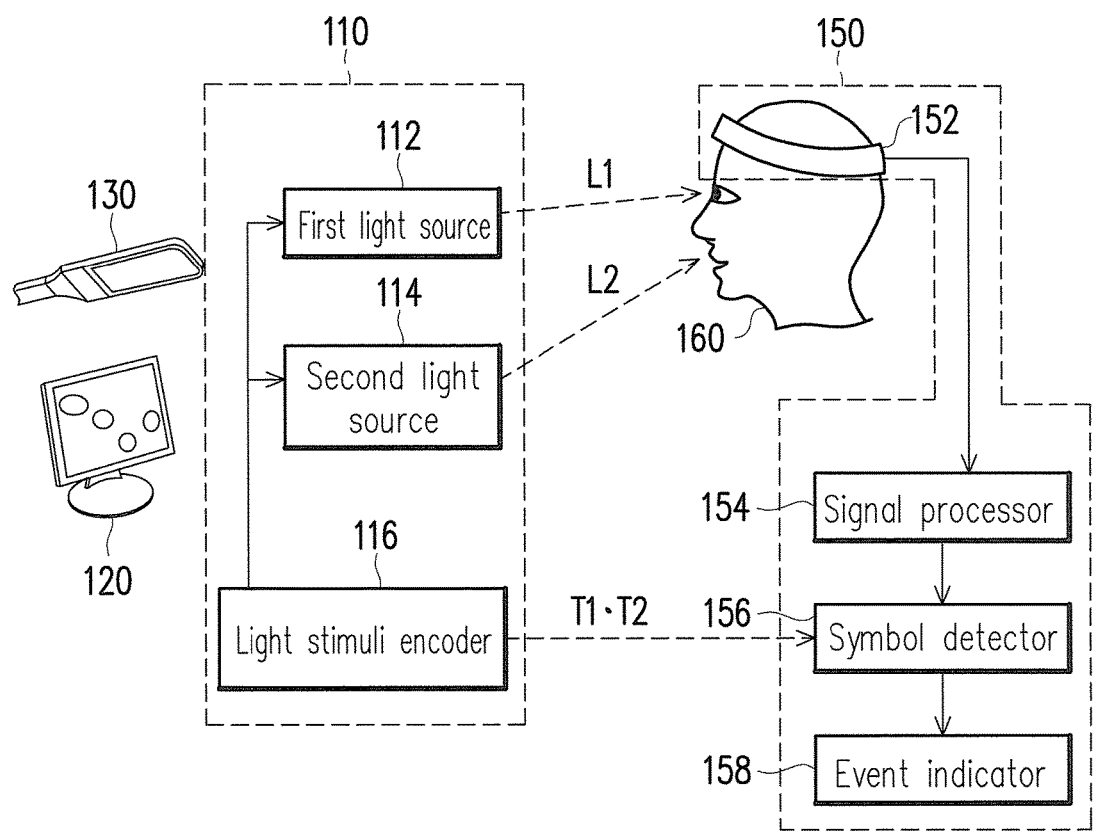
FIG. 1 is a schematic diagram illustrating a control system 100 for visual evoked responses according to an embodiment of the present invention.

FIG. 1 is a schematic diagram illustrating a control system 100 for visual evoked responses according to an embodiment of the present invention. The control system 100 includes a stimuli-generating device 110 and an EEG sensing device 150. stimuli-generating device 110 includes a first light source 112 and a second light source 114. The first light source 112 is configured to generate a first light L1 with a first wavelength, and the second light source 114 is configured to generate a second light L2 with one or more second wavelengths differing from the first wavelength. In the present embodiment, the second light L2 generated by the second light source 114 may be a combination of a plurality of lights with wavelengths differing from the wavelength of the first light L1. That is to say, the second light source 114 may be a composite light source. The combination effect of the light sources may maintain the colorfulness and brightness of the light sources and hue of the embedding images. The wavelengths of the first light L1 and the second light L2 fall within a human visual range, and the first wavelength and the second wavelength have different values. That is to say, a color displayed by the first light L1 is different from a color displayed by the second light L2. In the present embodiment, the stimuli-generating device 110 may have two or more light sources to generate light sources 112 and 114 having different wavelengths. Herein, the first light L1 and the second light L2 are collectively referred to as a stimuli light signal.

In an exemplary embodiment of the present invention, light-emitting diodes (LED) serving as red/green/blue light sources may generate irradiation spectrums that are quite approximate to original light wavelengths and thus, may adaptively serve as the light sources 112 and 114 of the embodiment of the present invention. In other embodiments, the stimuli-generating device 110 may be a display apparatus 120 using a light-emitting diode (LED), an organic light-emitting diode (OLED), a quantum dot light-emitting device (QD-LED) or the like as a backlight module or a lighting apparatus 130 fabricated by utilizing the aforementioned techniques.

In other words, the stimuli-generating device 110 of the present embodiment may be classified into two types according to application characteristics. A first type of stimuli-generating device 110 may be used not for the purpose of displaying images or may have an indication, illumination or display light source system with low resolution. With lights emitted through indirect illumination or directly by light-emitting sources, a viewer's vision is simulated by the stimuli light signal hidden in the light sources to generate the SSVEP. A second of stimuli-generating device 110 may by applied to a display apparatus for displaying high-resolution videos and display images, such as a liquid crystal display (LCD), an OLED display, a plasma display, a microelectromechanical (MEMS) display, a wearable visual display and so on. The wearable visual display may be, for example, a pair of Google Glasses or a watch display apparatus. In an example where an LCD serves as the stimuli-generating device 110, a panel of the LCD may employ an LED regional controlled backlight together with a liquid crystal layer in the LCD, such that a encoding technique may be employed by the embodiments of the present invention to control the lights to simulate the viewer and achieve advantages of the display screen, such as having high color saturation, high contrast and being power-saving.

The stimuli-generating device 110 flashes stimuli lights with specially adjusted amplitudes, waveforms and flickering frequencies according to the embodiments of the present invention, such that the combination of the lights leads the viewers to minimal or no flickering perception towards the light sources of the stimuli-generating device 110. When the stimuli lights are embedded into image displays, such as LCDs and OLEDs, etc., wavelengths, amplitudes and pulse widths/duty cycles of the stimuli lights are fine-tuned, so that the visual stimuli lights do not distort the original color images. The combined effect of the light sources should maintain the colorfulness and the hue of their embedding images. The visual or photic stimuli provided one or more viewers neither causes any discomfort nor introduces any pathological side effects such as migraine or seizure attacks to the one or more viewers.

In the present embodiment, the stimuli-generating device 110 further includes a light stimuli encoder 116. The light stimuli encoder 116 is coupled to the first light source 112 and the second light source 114 and configured to respectively modulate frequencies and amplitudes of the first light L1 and the second light L2, such that an average of energies generated by the first light L1 and the second light L2 per cycle is equal to a predetermined energy value of each of the first light L1 and the second light L2. In other words, the light stimuli encoder 116 of the present embodiment contains a digital encoder and a analog modulator to generate pulse-width modulation PWM signals of the first light L1 and the second light L2 to the light sources 112 and 114. The PWM signals may modulate parameters of the first light L1 and the second light L2, such as amplitudes, start times, pulse-widths, waveforms and so on, so as to serve as the stimuli light signals used by the control system 100 to induce visual evoked responses. In the present embodiment, a duty cycle of the first light is less than a duty cycle of the second light, a highest energy amplitude of the first light L1 is greater than a highest energy amplitude of the second light L2, and an average of energies generated by the first light L1 and the second light L2 per cycle is equal to a predetermined energy value of each of the first light L1 and the second light L2. Detailed description with respect to the modulation of the first light L1 and the second light L2 will be clearly set forth in the embodiments below.

The EEG sensing device 150 includes an electroencephalography EEG sensor 152, an EEG signal amplifier, a signal processor 154, a symbol detector 156 and an event indicator 158. The EEG sensor 152 is formed by at least one electrode and configured to sense, capture and record SSVEP signals/SSVEP responses of a viewer 160. It is to be mentioned that when the stimuli lights emit to the viewer with his/her eyes closed, may be directly stimulated by the stimuli lights due to a light-transmission effect, and SSVEP responses are accordingly produced from the viewer's brain. A sensor applied to a research instrument, a clinical equipment or a consumer device may be correspondingly selected and used as the EEG sensor 152; however, the sensor applied to the consumer device may yield less reliable SSVEP due to poorer signal quality. Persons who apply the present embodiment may correspondingly select an EEG sensor with adaptive sensitivity. The EEG signal amplifier may be disposed in the EEG sensor 152 and coupled to the at least one electrode on the EEG sensor 152. The SSVEP of a human brain is relatively weak, and thus, an EEG signal of the viewer 160 needs to be amplified by employing the EEG signal amplifier when the viewer 160 is simulated by the first light and the second light.

The signal processor 154 is coupled to the EEG signal amplifier and configured to reduce noise in the EEG signal. Since the EEG signal is low in its amplitude, in the embodiments of the present invention, a plurality of signal analysis techniques including principal component analysis (PCA), independent component analysis (ICA) and canonical correlation analysis (CCA) may be employed to boost SNR values of the SSVEP signals. Persons who apply the present embodiment may boost the SNR values of the SSVEP signals by employing a plurality of signal analysis techniques that is well known in the art to enhance the characteristics for sensing the SSVEP signals without being limited in the aforementioned signal analysis techniques.

The symbol detector 156 is coupled to the signal processor 154 and configured to decode the EEG signal according to the frequency of the first light source and the frequency of the second light source or clock signals T1 and T2 so as to generate a decoded signal. In other words, the symbol detector 156 serves purposes of ensuring robust detection of the SSVEP signals and decoding the display with embedded digital symbols according to the frequencies (i.e., the clock signals T1 and T2) of the first light source and the second light source generated by the stimuli-generating device 110 so as to obtain decoded signals. In the present embodiment, the clock signals T1 and T2 may be PWM signals may be transmitted from the light stimuli encoder 116 to the light sources 112 and 114. The event indicator 158 is coupled to the symbol detector 156 and configured to receive the decoded signal and generate a brain analysis result of the viewer 160 according to the decoded signal. The event indicator 158 may determine the brain state of the viewer 160 by utilizing the decoded information and respond with respect to the brain state being classified. Accordingly, the event indicator 158 plays an important role in both the control system 100 and linking to related applications.

After each element and the related function of the control system 100 of the present embodiment is described, description will be made with respect to how each of the first light L1 and the second light L2 generated by the light sources 112 and 114 is modulated, such that the human eyes imperceptibly perceive the flickers of stimuli light signals of the control system 100, and the stimuli light signals may be encoded into videos, images and illumination lights of a display. In the present embodiment, in order to induce the human eyes to imperceptibly perceive the flickers of the stimuli light signals, a light frequency of a stimuli light signal (i.e., the combination of the lights L1 and L2) has to be approximate to or higher than a critical fusion frequency (CFF) of human vision. A high-frequency stimuli light signal may induce the viewer 160 to obtain a SSVEP signal with a high signal-to-noise ratio (SNR) under the stimuli with imperceptible flickers. In the present embodiment, the red/green/blue light sources commonly used in the display are illustrated for example, and the person who applies the present embodiment may adjust light colors by modulating light wavelengths as needed. However, a yellow light source and a white light source, for example, may also be employed in the illumination system according to the embodiments of the present invention, and thus, the present invention is not limited to using only the aforementioned light colors. Under the stimuli from the lights at 85 cd/m$^2$ intensity and a duty cycle of 10%, CFF thresholds of the red, green and blue lights are 30 Hz, 50 Hz and 35 Hz, respectively. It is to be specially mentioned that in the embodiments of the present invention, the combination of two or more lights with different wavelengths serves as stimuli lights. It can be known according to experiments that when the red, green and blue lights are combined respectively at the frequencies of 20 Hz, the human eyes recognize the combination of the lights as continuous images and imperceptibly perceive the flickers. Accordingly, the stimuli lights of the embodiments of the present invention may employ the lowest CFF threshold of 20 Hz, while the highest frequency for the stimuli light is not limited.

Thus, when illuminating with multi-color lights, a flickering frequency of each color light may be set to be higher than the CFF threshold (i.e., 20 Hz) so as to mitigate the visual flickers as many as possible. Nevertheless, amplitude of a SSVEP signal is inversely proportional to a light frequency of a stimuli light signal. In order to enhance the sensitivity to the SSVEP signal, the frequencies, the energy amplitudes, the duty cycles of the first light L1 and the second light L2 are modulated when the frequencies of the stimuli light signal are higher than the CFF threshold so as to obtain preferable sensitivity to the SSVEP signals according to the embodiments of the present invention. In the present embodiment, even though the light frequency independently generated by each light source is lower than the CFF threshold of each light wavelength, flickering frequency of the combination of the two or more lights is above the CFF threshold of each light wavelength so as to eliminate the flickering for the viewer. For instance, when the red/green/blue light sources independently generate three color lights, i.e., red/green/blue lights, respectively at a frequency of 20 Hz, the light frequency of the combination of the red/green/blue lights will be 3 times of 20 Hz, i.e., 60 Hz, which is above the CFF threshold.

Figure 2:
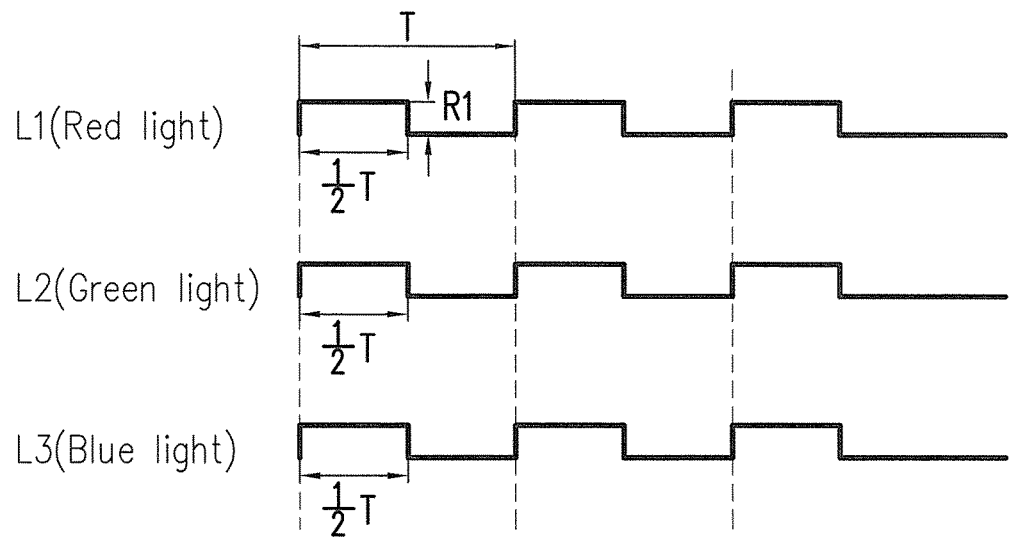
FIG. 2 is a schematic diagram illustrating waveforms of red/green/blue light sources emitted by a general display device.
Figure 3A:
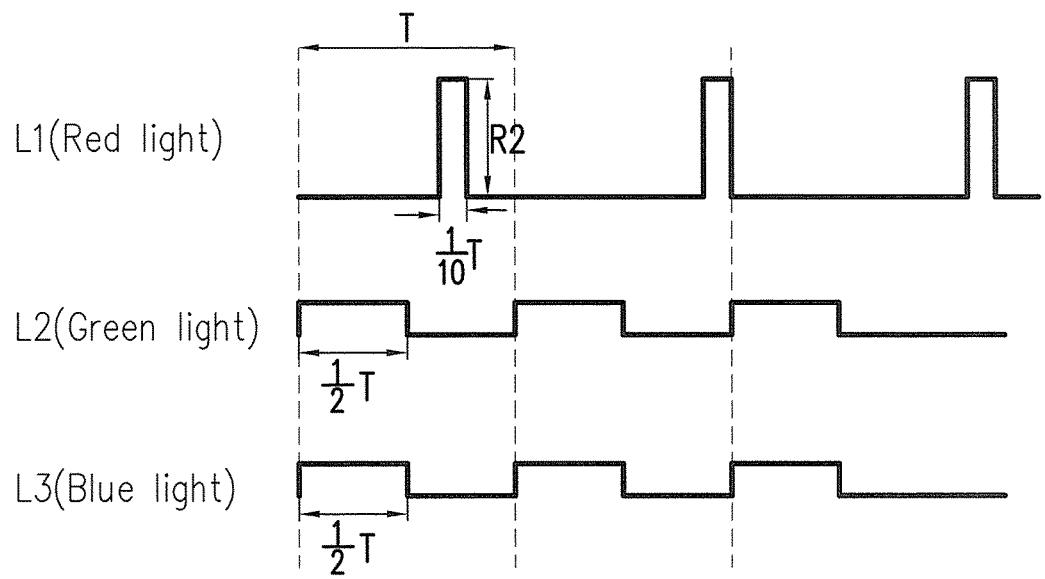
FIG. 3A and FIG. 3B are schematic diagrams respectively illustrating waveforms of the first light L1, the second light L2 and the third light L3 emitted by the stimuli-generating device 110 according to an embodiment of the present invention.
Figure 3B:
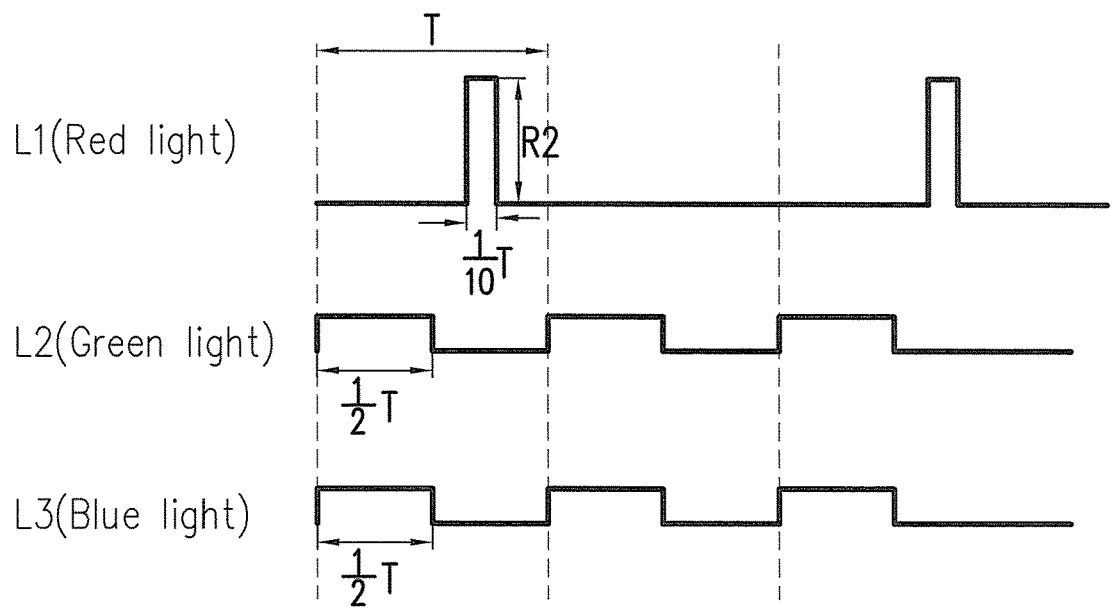

Hereinafter, description will be made with respect to how the frequencies, the energy amplitudes, the duty cycles of the first light L1 and the second light L2 are modulated to obtain preferable sensitivity to the SSVEP signals. Here, a display device 120 with red/green/blue backlight modules is illustrated as an example of the stimuli-generating device 110, where the first light L1 and the second light L2 are square waveforms. FIG. 2 is a schematic diagram illustrating waveforms of red/green/blue light sources emitted by a general display device, and FIG. 3A and FIG. 3B are schematic diagrams respectively illustrating waveforms of the first light L1, the second light L2 and the third light L3 emitted by the stimuli-generating device 110 according to an embodiment of the present invention. The first light L1, the second light L2 and the third light L3 respectively correspond to the red light, the green light and the blue light, and the person who applies the present embodiment may adaptively adjust according to actual applications. With reference to FIG. 2 and FIG. 3, each cycle is labeled as T. In the present embodiment, if only the frequencies of the lights L1 through L3 is increased to be higher than the CFF threshold, without modulating the duty cycles and the amplitudes of the lights L1 through L3, it may result in difficulty in sensing the SSVEP signals due to the inversely proportional relationship between the amplitudes of the SSVEP signals and the frequencies of the stimuli light signals. For instance, in FIG. 2, if it is assumed that the frequency of each of the lights L1 through L3 is still 60 Hz, and the duty cycle of each of the lights L1 through L3 is 50%, an enablement time period for each of the lights in each cycle T is (½) T.

Thus, in FIG. 3A, in order to make the simulation of the lights L1 through L3 more sensible to the viewer to respond to SSVEP signals, the light stimuli encoder 116 of the embodiments of the invention modulates the duty cycles, the highest energy amplitudes and the frequencies of the lights L1 through L3, and even a phase relationship among them. Referring to FIG. 3A, if it is assumed that the frequency of each of the lights L1 through L3 is still 60 Hz, the duty cycle of the first light L1 (the red light) is modulated as 10%, and namely, the enablement time for the first light L1 in each cycle T is (¹⁄₁₀) T, such that the duty cycle (10%) of the first light L1 is less than the duty cycles (50%) of the lights L2 and L3. Moreover, due to the persistence of vision in human eyes, the images perceived by the viewer is the brightness (the energies) of the lights averagely distributed at each cycle time when viewing light signals (e.g., videos or images) which do not flicker. Therefore, in order to balance the brightness in each cycle T, the highest energy amplitude of the first light L1 is greater than its original energy amplitude. In the present embodiment, if in each cycle T, the brightness energy to be generated by the first light L1 (the red light) is equal to a predetermined energy value of the red light, a highest energy amplitude R2 the first light L1 depicted in FIG. 3A is equal to 5 times a highest energy amplitude R1 of the first light L1 depicted in FIG. 2 due to the adjustment of the duty cycle. The light stimuli encoder 116 may further enable the duty cycle of the first light L1 and the duty cycles of the second and the third lights L2 and L3 at different times, as illustrated in FIG. 3A. Thus, since the duty cycle of the first light L1 is shortened and the highest energy amplitude R2 thereof is increased, the first light L1 will have a waveform shape different from waveform shapes of the lights L2 and L3, and as a result, the SSVEP signal may be sensed more easily.

Referring to FIG. 3B, the embodiment illustrated in FIG. 3B is similar to the embodiment illustrated in FIG. 3A and different therefrom in the frequency of the first light L1 being modulated to be 30 Hz from original 60 Hz, which leads the duty cycle of the first light L1 to being enabled once per two cycles from once per cycle. Therefore, when the duty cycle of the first light L1 is enabled, the highest energy amplitude R2 of the first light L1 has a greater value due to the predetermined energy value of the red light, which results in the waveform shape of the first light L1 being much different from the waveform shapes of the lights L2 and L3. Accordingly, stimuli light signals embedded into an LCD backlight panel and an LCD color image filter may be similar to the lights L1 through L3, in which visual stimuli with imperceptible flickers are embedded by intersecting normal pulses (the lights L2 and L3) with a sharp pulse (the light L1). Likewise, a contrast between the amplitude ratios and the energy ratios of the light pulses shall be increased as much as possible to induce strong SSVEP responses. The LCD panel generally displays visual images by using a variety of colors and brightness, and thus, the visual stimuli embedded into the color images must not influence the fidelity of the images. Therefore, not only the perception of the stimuli flickering lights to the human eyes has to be overcome, but also the acuity, the contrast and the hue of the visual images have to be maintained after the stimuli lights are embedded into the visual images. When using the similar pulse-width modulation (PWM) signals for brightness control, the light stimuli encoder 116 modulates the brightness of each color component (or the average energy amplitude) with a stimuli pulse having a narrow width and a normal pulse having a wide width.

Figure 3C:
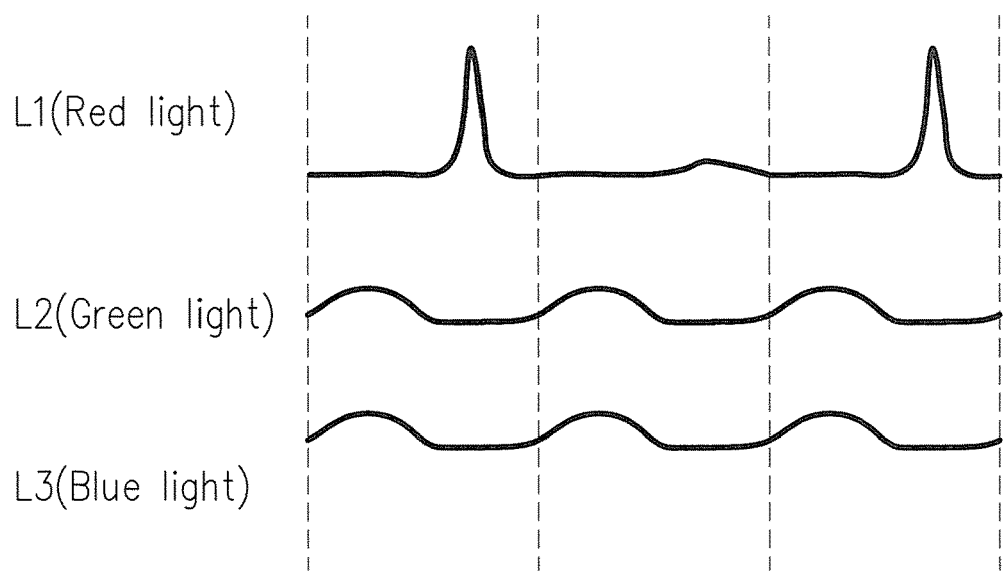
FIG. 3C is a schematic diagram illustrating the waveforms of the first light L1, the second light L2 and the third light L3 which are modulated by employing cosine waveforms according to an embodiment of the present invention.

With reference to FIG. 3A and FIG. 3B, square waveforms are employed to modulate the lights L1 through L3, such that the SSVEP signal may be sensed more easily in a time domain. However, in order to make the SSVEP signals to be detected more easily, a cosine waveform may also be used to modulate the lights L1 through L3 according to the embodiments of the present invention. The stimuli-generating device 110 may employ smooth waveforms with limited time/space/frequency rang, such as raised waveform, Hanning waveforms and tapered cosine waveforms in replacement with the rectangular pulses/square waveforms employed in the above. In other words, a waveform generated by each of the lights L1 through L3 in each duty cycle may be one of a square waveform and a cosine waveform. FIG. 3C is a schematic diagram illustrating the waveforms of the first light L1, the second light L2 and the third light L3 which are modulated by employing cosine waveforms according to an embodiment of the present invention. The embodiment illustrated in FIG. 3C is similar to that in FIG. 3B and different therefrom in the light stimuli encoder 116 modulating the lights L1 through L3 by using cosine waveforms, such that the SSVEP signals may be sensed more easily in a frequency domain to suppress the amplitudes of the SSVEP signals in harmonics and improve the accuracy and robustness of signal detection. Additionally, an average of the energy of the first light L1 per cycle is equal to its predetermined energy value or has a proportional relationship to its predetermined energy value. The predetermined energy values and their related ratio parameters may be obtained by employing adequate times of experiments according to the point of view of the technicians in the art.

It is to be specially mentioned that the lights L1 through L3 of FIG. 3A through 3C are merely illustrated as examples of the embodiments of the present invention. The persons who apply the present embodiment may adjust the duty cycles and the highest energy amplitudes of the lights L1 through L3 as well as the phase difference among the lights L1 through L3, as needed. In other words, the duty cycles of the lights L2 and L3 may be 50%, 60%, 80%, 100% and so on, while the duty cycle of the light L1 may also be adjusted as 10%, 20%, 50% and so on. The number of the lights may also not be limited to the three types of lights L1 through L3 illustrated in FIG. 3A~3C, and the combination and the encoding of the parameters, such as the frequencies, the amplitudes, the phases, of two or more lights may be employed to implement the stimuli light signals of the embodiments of the present invention. Therefore, the first light, the second light and the third light of the embodiment of the present invention are not limited in the aforementioned embodiment.

Figure 4:
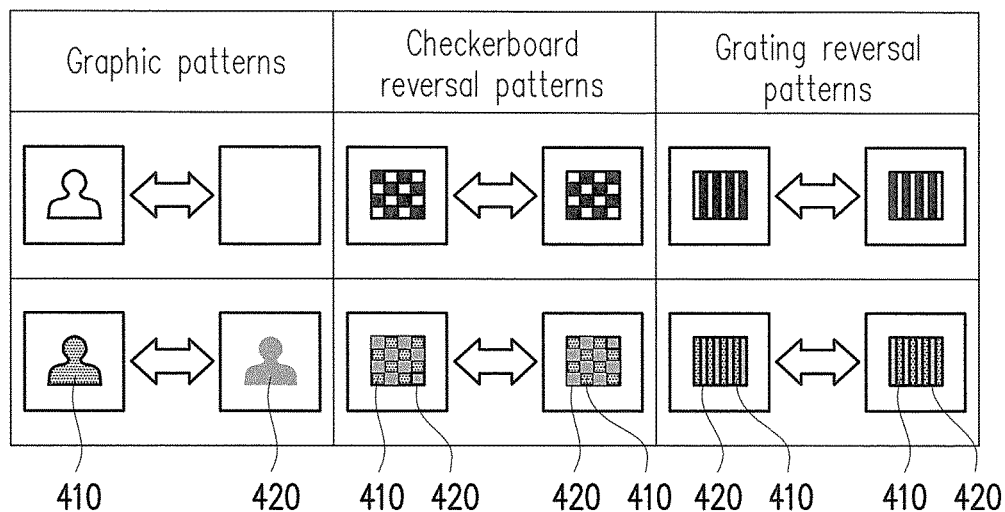
FIG. 4 is a schematic diagram illustrating patterns according to an embodiment of the present invention.

If an illumination system serves as the stimuli-generating device 110, the stimuli-generating device 110 may emit sharp light pulses (light energies) to implement the techniques described above. The stimuli light signals with imperceptible flickers may maintaining a modest proportion between the energy in a stimulating pulse and the energy in a normal pulse by increasing the amplitude of certain stimulating light pulses while reducing the operating bandwidth in the light pulses. Since the light-sensitivity of the illumination system is proportional to the average energy in the light pulses, while the SNR of the SSVEP signals is also proportional to the amplitude of the light pulses, stronger SSVEP signals can be induced by increasing the contrast between the amplitude ratios and the energy ratios among the stimulating pulses and the normal light pulses. In the embodiments of the present invention, spatial patterns may also be added to the imperceptible stimuli in visual flickers to improve the SSVEP signals and the SNR values, as illustrated in FIG. 4. FIG. 4 is a schematic diagram illustrating patterns according to an embodiment of the present invention. On the first row in FIG. 4, black-and-while patterns (including graphic patterns, checkerboard reversal patterns, grating reversal patterns from the left to the right) are illustrated, which have been widely applied to the stimuli of low-frequency SSVEP signals. On the second row in FIG. 4, color patterns are illustrated, which emphasize the effectiveness produced by two types of color lights to the SSVEP signals of the viewer's brain. The two color lights may have complementary colors or opponent colors. Taking the complementary color lights for example, the alternately flickering complementary color lights present gray scales with different brightness levels in the viewer's eyes so as to mitigate the influence caused by the stimuli to image hue. That is to say, in the color lights that are complementary to each other, a stimuli color light 410 may be one of the basic red, blue and green color lights, while another type of stimuli color light 420 has a complementary color to the stimuli color light 410. Said another type of stimuli color light 420 may be a composite color light from two types of color lights. On the other hand, taking the opponent color lights for example, since two different color lights are easily distinguished (for example, neither a light-green light may be viewed in a red light nor mastic light can be viewed in a blue light) in human vision when viewing the opponent color lights, better SSVEP signals will be obtained if employing the opponent color lights as the stimuli light signals for the color patterns illustrated on the second row in FIG. 4. For instance, the stimuli color light 410 may be a red light or a yellow light, while the other stimuli color light may be a opponent color light to the stimuli color light 410, such as a green or blue light. In other words, the first light source and the second light source illustrated in FIG. 1 may be disposed on different light-emitting positions to arrange the patterns as illustrated in FIG. 4 so as to obtain better SSVEP responses. It is apparent to the persons who apply the embodiment the present embodiment that the patters illustrated in FIG. 4 are merely three examples among various types of patterns, and the present invention is not limited thereto.

Figure 5:
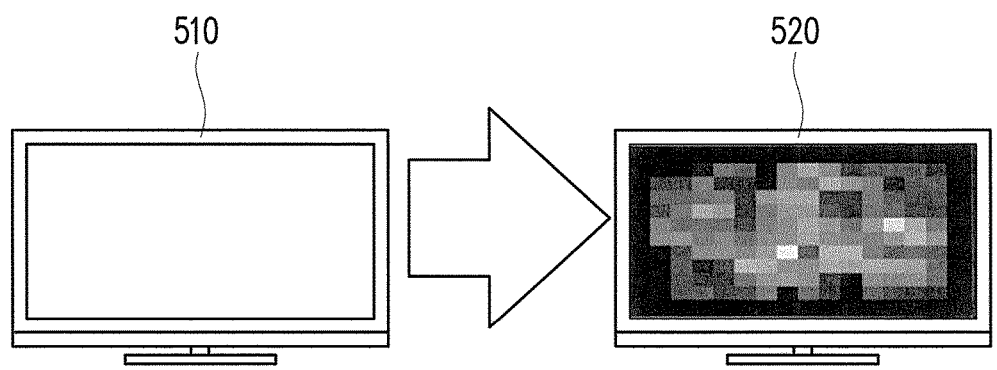
FIG. 5 is a schematic diagram illustrating a display according to an embodiment of the present invention.

It is to be mentioned that when serving a display as the stimuli-generating device 110, the visual simulation to the viewer is typically achieved by employing specific spatial brightness distribution and flickering patterns. Therefore, in the display of the present embodiment, brightness and chroma of a part of the display may be adjusted in each block of the backlight module. FIG. 5 is a schematic diagram illustrating a display according to an embodiment of the present invention. For example, a display 510 illustrated on the left of FIG. 5 has the same brightness and chroma in each region thereof, while a display 520 illustrated on the right of FIG. 5 has different brightness and chroma in each region thereof. Thereby, different regions on the display may produce different flickering light signals to achieve and effect of partially controlling the light sources, as illustrated in FIG. 5. In the embodiments of the present invention, flickering patterns or flickering light signals may be embedded into different regions on the display, such that which region on the display the viewer's sight is in may be recognized, and thereby, time-line visual orientation recognition and visual control techniques may be achieved. Additionally, when unrelated flickering patterns are embedded into the peripheral region, it helps to mitigate the flickering degree of entire display. Spatial brightness distribution of each localized lighting region can also be configured independently through the adjustment of the brightness and hue, and circular spatial symmetry and smooth brightness distribution facilitates in reducing spatial crosstalk and enhancing the SSVEP responses.

Figure 6A:
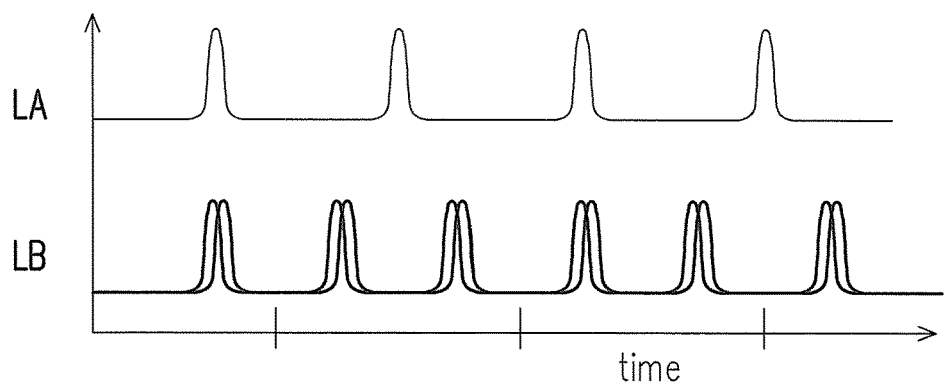
FIG. 6A through FIG. 6C are schematic diagrams of encoding the stimuli lights according to an embodiment of the present invention.
Figure 6B:
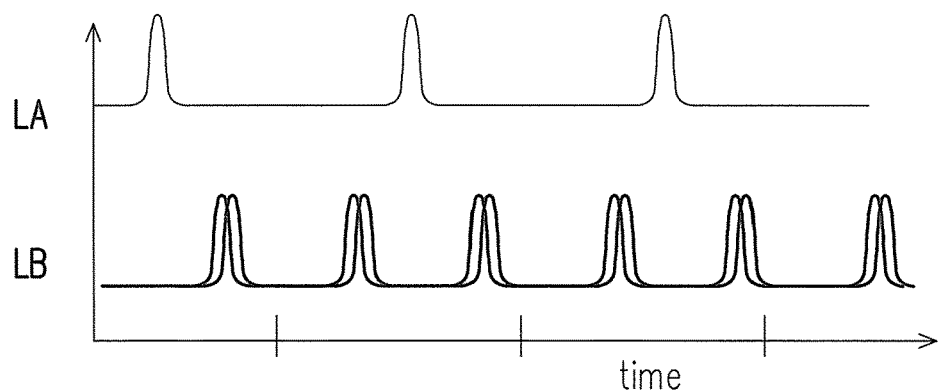
Figure 6C:
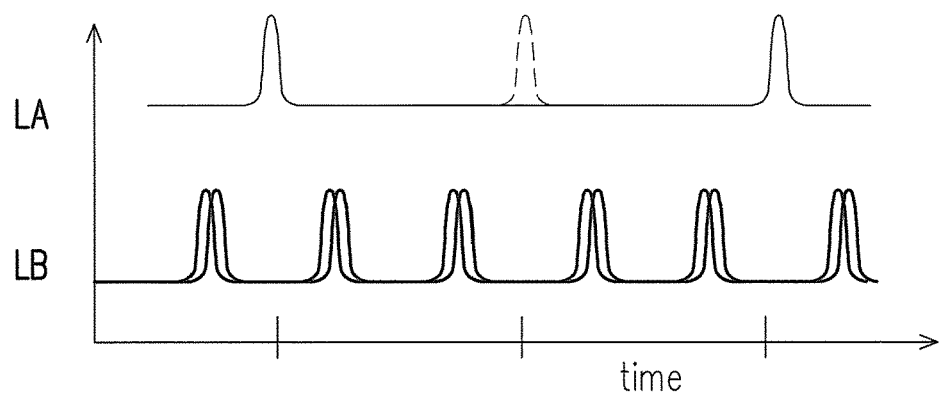

In the embodiments of the present invention, when the stimuli lights are encoded, frequency/phase/sequence coding techniques may be utilized to embed required digital codewords into the stimuli light signals. FIG. 6A through FIG. 6C are schematic diagrams of encoding the stimuli lights according to an embodiment of the present invention, and therein, a light signal LA represents an uncoded signal waveform, while a light signal LB represents an encoded signal waveform. In the frequency coding technique (referring to FIG. 6A), the stimulating flickering lights at different frequencies are used in each stimuli light signal, which means that each light is synchronously enabled, and SSVEP response is induced by employing the difference between each of the lights at different frequencies. In the phase coding technique (referring to FIG. 6B), the SSVEP responses are induced by employing phase difference between each of the stimulating flickering lights at a fixed frequency in the stimuli light signal during an enablement period. In the chip sequence coding technique (referring to FIG. 6C), orthogonal code division multiplexing (OCDM) sequences may be embedded to encode the stimuli light signal. The use of OCDM sequences enables the visual stimuli viewed by the viewer to be sharper and clearer, reduces power consumption, improves probability of success for decoding the SSVEP signals, and enhances the information transfer rate (ITR) of the SSVEP signals.

Figure 7A:
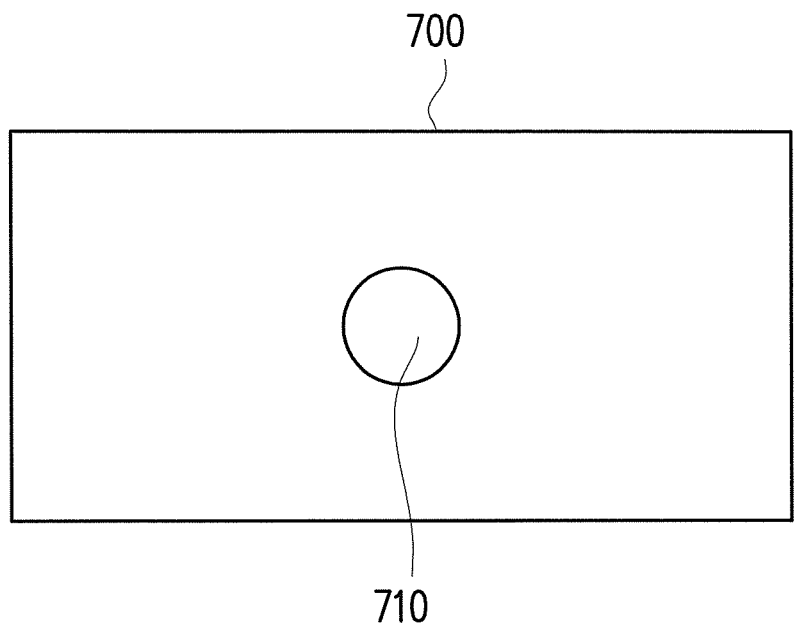
FIG. 7A and FIG. 7B are schematic diagrams illustrating light projection experiments performed on a central region and an annular region according to an embodiment of the present invention.
Figure 7B:
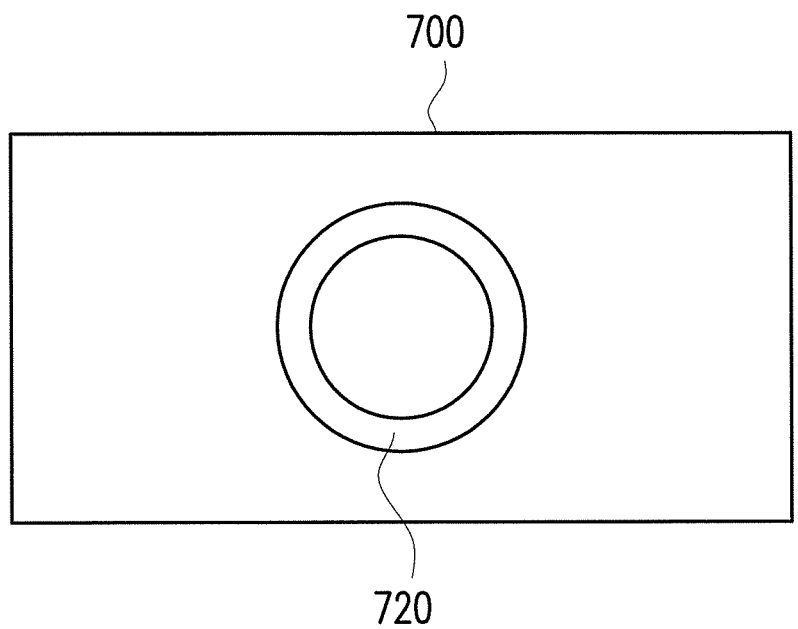
Figure 8:
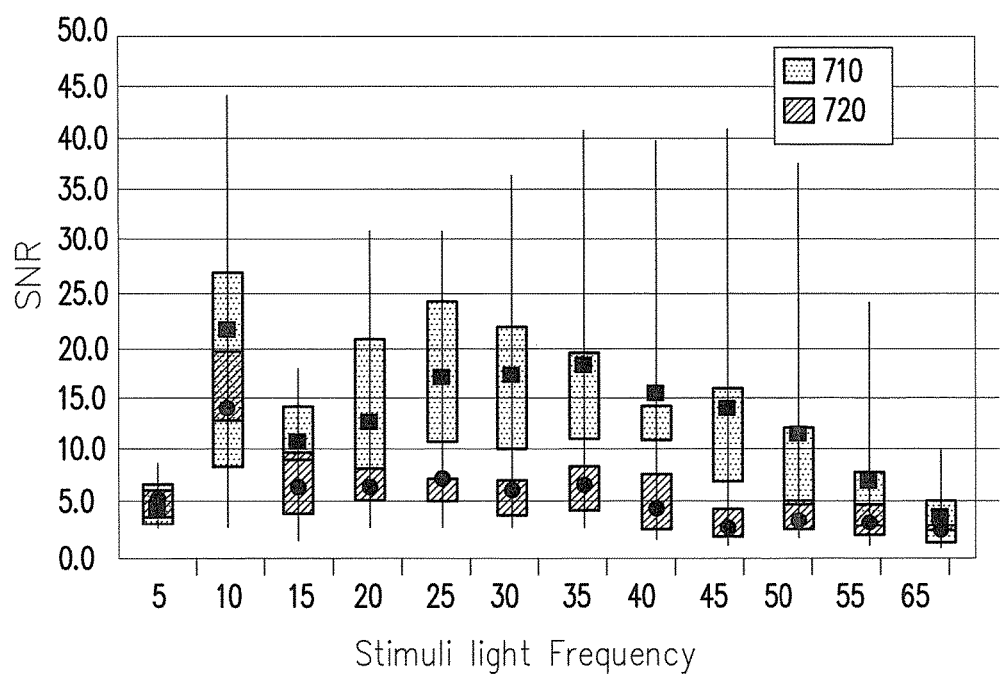
FIG. 8 is a graph illustrating a relationship between signal-to-noise ratios (SNR) of the steady-state visual evoked potential (SSVEP) signals generated by the viewer and the frequencies of the stimuli lights used by the experiments illustrated in FIG. 7A and FIG. 7B.

In order to estimate optimal stimuli lights and stimuli patterns for the viewer, a central region 710 of a display 700 are employed to emit stimuli lights, as illustrated in FIG. 7A, and an annular region 720 in the periphery of the display 700 are employed to emit stimuli lights, as illustrated in FIG. 7B so as to estimate the SSVEP responses of the viewer. FIG. 7A and FIG. 7B are schematic diagrams illustrating light projection experiments performed on the central region and the annular region according to an embodiment of the present invention. In FIG. 7A, the stimuli lights are merely emitted from the central region 710, while in FIG. 7B, the stimuli lights are merely emitted from the annular region 720, and inside the annular region 720 is a dark region. FIG. 8 is a graph illustrating a relationship between SNR of the SSVEP signals generated by the viewer and the frequencies of the stimuli lights used by the experiments illustrated in FIG. 7A and FIG. 7B. Therein, the dotted distribution region represents actual data from the experiment depicted in FIG. 7A, while the slashed distribution region represents actual data from the experiment depicted in FIG. 7B. Accordingly, when emitting the stimuli lights merely from the central region 710, the stimuli lights has not bad SNR values when being at frequencies from 20 Hz to 65 Hz, and better SNR values when being at frequencies from 25 Hz to 45 Hz. Thereby, it is known that the better frequencies shall be at the range from 25 Hz to 45 Hz.

The embodiments of the present invention may be applied to a plurality of fields, such as an eye tracking system, a brain-computer interaction (BCI) system, a monitoring system, and medical assessment systems for diseases, e.g., migraine and epilepsy. Taking the eye tracking system for example, in the embodiments of the present invention, the stimuli lights are emitted on a display or a windshield by employing encoded backlights and footlights. Since persons (e.g., nuclear control room operators, airplane pilots, tank/truck drivers and production line control staffs, who operate the eye tracking system may have to gaze at different monitoring screens alternately, they may utilize the present invention to confirm users' operation states or generate corresponding operation commands based on the operators' gaze sights.

Figure 9:
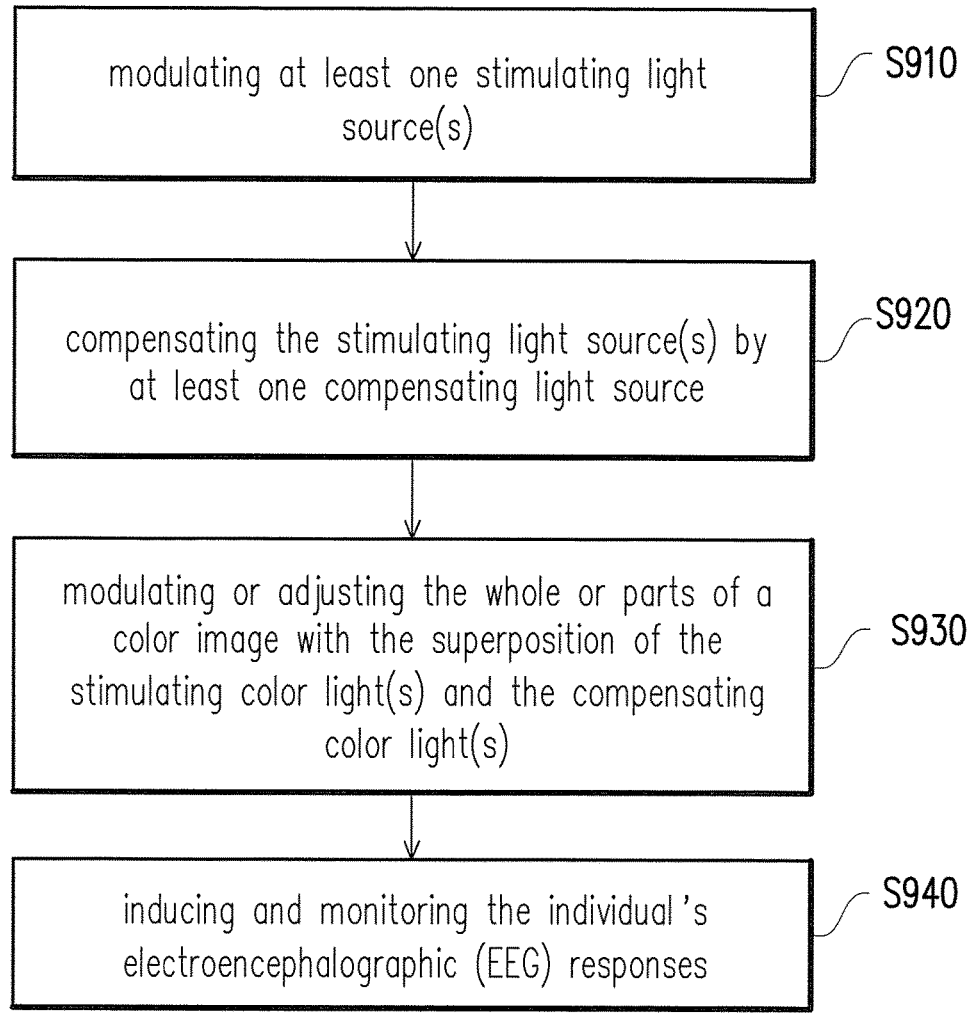
FIG. 9 is a flowchart illustrating a method to induce visual evoked potentials using imperceptibly flickering multi-color lights according to an embodiment of the present invention.

According to another aspect, the present provides a method to induce visual evoked potentials using imperceptibly flickering multi-color lights, which is applicable to the control system depicted in FIG. 1. FIG. 9 is a flowchart illustrating the method to induce visual evoked potentials using imperceptibly flickering multi-color lights according to an embodiment of the present invention. Referring to both FIG. 1 and FIG. 9, in step S910, the light stimuli encoder 116 generates a first light L1 with a first wavelength by using the first light source 112. The first light L1 is at a frequency higher than the CFF threshold of human vision. In step S920, the light stimuli encoder 116 generates a second light L2 with one or more second wavelengths differing from the first wavelength by using the second light source 114. The second light L2 is also at a frequency higher than the CFF threshold of human vision. Additionally, a duty cycle of the first light L1 is less than a duty cycle of the second light L2, a highest energy amplitude of the first light L1 is greater than a highest energy amplitude of the second light L2, and an average of energies generated by the first light L1 and the second light L2 per cycle is equal to a predetermined energy value of each of the first light L1 and the second light L2. Meanwhile, in step S930, whether the viewer 160 is stimulated by the first light L1 and the second light L2 is determined. If yes, step S940 is entered, and the EEG sensing device 150 receives an EEG signal of the viewer 160 through the at least one electrode and analyzes the EEG signal. Related technical contents of the method of the present embodiment may refer to the embodiments above and will not be repeated hereinafter.

The following description of the embodiments also can be achieved the spirits of the present invention. A method to imperceptibly alter an individual's brain state and/or induce measurable responses of the individual's neural cortices is provided in the embodiment of the present invention. The method comprises: modulating flickering of at least one stimulating light source to induce a desired neural response or specific change of the individual brain state; wherein the flickering is imperceptible to the individual being compensated by at least one compensating light source, wherein each of the compensating light sources are composed of one or more color light(s) with specific or randomized spatial luminance distributions and temporal waveforms. Each stimulating light source comprises one or more color light(s), each of which has a specific wavelength, a special spatial luminance distribution and a specific temporal waveform along with a specific flickering frequency, amplitude and/or phase to serve the purpose of inducing specific neural responses and/or causing specific changes of brain states of the individual. The method further comprises: monitoring a color image onto which the stimulating light is superimposed, wherein each color light of the compensating light has a spatial luminance distribution and temporal waveform that compensates the stimulating light source in order to preserve the hue, the colorfulness and the general display effects of the color image. The method further comprises: modulating each color light of the compensating light has a spatial luminance distribution and a temporal waveform that compensates the stimulating light source to preserve the hue and the colorfulness of the color image.

The stimulating light source generates light pulses with shorter pulse durations (or duty cycles), higher amplitudes and/or lower flickering frequencies than the pulse duration, amplitude and/or flickering frequency of the compensating light sources. The light pulses from the stimulating light source(s) and those from the compensating light(s) may be offset or asynchronous from one another. The light pulses are manipulating by smoothing the waveforms, so that the power of the light pulses is concentrated in a narrow range of frequencies. The stimulating light sources and the compensating light sources appear alternating in the same spatial positions and form spatial patterns across a lighting surface. The stimulating light source or the compensating light source(s) may alternate at the lowest flickering frequency among all light sources while the flickering frequencies of the other light sources are a multiple of that alternating frequency. The combined flickering frequency of the stimulating and compensating light sources may lie above the critical flicker fusion threshold (CFF) of the composite of the stimulating light source and the compensating light source. An average power of the stimulating light source and the compensating light source may maintain the proper ratios that keep the correct balance of the hue and the colorfulness of the color image. The stimulating light source and/or compensating light source may be modulated with stimulating patterns or digital codes by means of frequency modulation, phase modulation or chip sequence modulation. The method may further comprises: inducing and monitoring the individual's electroencephalographic (EEG) responses.

Another control system is presented in the embodiment of the present invention. The control system comprises a computer-usable medium having a computer-readable program code embodied therein. The computer-readable program code adapts to be executed to implement a method to imperceptibly alter an individual's brain state and/or induce measurable responses of the individual's neural cortices. The control system comprises: logic configured to modulate the flickering of at least one stimulating light source to induce a desired neural response or specific change of the individual brain state; wherein the flickering is imperceptible to the individual being compensated by at least one compensating light source, wherein each of the compensating light sources are composed of one or more color light(s) with specific or randomized spatial luminance distributions and temporal waveforms.

The control system may further comprising: logic to control the spatial-temporal characteristics of the stimulating and the compensating lights as well as their timing relations; logic to monitor the responses and the states of the individuals' brains through electroencephalographic (EEG) signal analysis or other indirect observation; and logic to provide feedback between the viewer monitoring system and the stimuli generating mechanisms or devices. The control system may further comprise a stimuli generating device and a brain state monitoring device. The control system may have an information feedback path between these two devices. The stimuli generating component may comprise a light stimuli encoder that is coupled to the stimulating and compensating light sources respectively to control the spatial-temporal characteristics of the stimulating and the compensating light source including flickering frequencies, amplitudes, relative phases, their temporal waveforms and spatial luminance distributions of the light sources.

Another stimuli generating device is presented in the embodiment of the present invention to imperceptibly alter an individual's brain state and/or induce measurable responses of the individual's neural cortices. The stimuli generating device may comprises: at least one stimulating light source composed of one or more color light(s), each of which has a specific wavelength, a special spatial luminance distribution and a specific temporal waveform along with flickering frequency, amplitude and phase to serve the purpose of inducing specific neural responses and/or causing specific changes of brain states of the human viewers; at least one compensating light source, each of which composed of one or more color light(s) with specific or randomized spatial luminance distributions and temporal waveforms to serve the purpose of compensating the stimulating light in order to preserve the hue, the colorfulness and the general display effects of the color image; and, a means for modulating the flickering of at least one stimulating light source to induce a desired neural response or specific change of the individual brain state; wherein the flickering is imperceptible through the compensation by at least one compensating light source.

The stimuli-generating methods, devices and control systems described in this disclosure may be implemented within or by one or more of a general purpose microprocessor, digital signal processor (DSP), application specific integrated circuit (ASIC), field programmable gate array (FPGA), programmable logic devices (PLDs), or other equivalent logic devices. Accordingly, the terms "processor" or "controller," as used herein, may refer to any one or more of the foregoing structures or any other structure suitable for implementation of the techniques described herein.

The various components illustrated herein may be realized by any suitable combination of hardware, software, firmware, or any combination thereof. In the figures, various components are depicted as separate units or modules. However, all or several of the various components described with reference to these figures may be integrated into combined units or modules within common hardware, firmware, and/or software. Accordingly, the representation of features as components, units or modules is intended to highlight particular functional features for ease of illustration, and does not necessarily require realization of such features by separate hardware, firmware, or software components. In some cases, various units may be implemented as programmable processes performed by one or more processors.

If implemented in software, the techniques may be realized at least in part by a computer-readable data storage medium comprising code with instructions that, when executed by one or more processors, performs one or more of the methods described above. The computer-readable storage medium may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), embedded dynamic random access memory (eDRAM), static random access memory (SRAM), flash memory, magnetic or optical data storage media. Any software that is utilized may be executed by one or more processors, such as one or more DSP's, general purpose microprocessors, ASIC's, FPGA's, or other equivalent integrated or discrete logic circuitry.

Various aspects have been described in this disclosure. These and other aspects are within the scope of the following claims.

To sum up, in the control system, the stimuli-generating device and the method to induce visual evoked potentials using imperceptibly flickering multi-color lights, the viewer's brain is induced to generate visual evoked responses by using the combination of two or more stimuli lights having different wavelengths and flickering frequencies. After the stimuli lights are modulated with various frequencies and energies, the stimuli lights may be easily encoded into videos, images and illumination lights of a display, such that the stimuli lights may be hidden in various types of display apparatuses and illumination systems and induce the viewer to generate visual evoked responses with high SNR. In the meantime, the frequencies of the lights and the frequency of the combination of the lights are approximate to or higher than the CFF threshold of human vision. Thereby, risks of causing any discomfort to the viewer may be significantly reduced so as to provide a brain-computer interaction technique which is safe, comfortable and capable of instantly and accurately sensing the EEG signals. The control system proposed in the embodiments of the present invention may be further combined with image transmission technology for achieving applications in fields for the viewer, such as visual tracking, visual manipulation, brain medical testing, industrial safety, human-computer interaction interface and so on.

Although the invention has been described with reference to the above embodiments, it will be apparent to one of the ordinary skill in the art that modifications to the described embodiment may be made without departing from the spirit of the invention. Accordingly, the scope of the invention will be defined by the attached claims not by the above detailed descriptions.

What is claimed is:

1. A method to induce measurable responses from neural cortices of a human viewer watching a displayed image or video, the method comprising:
retrieving an image or video from a data storage medium;
selecting a region of the image or video to display a combination of colored light pulses, wherein the selected region is less than the entire image or video;
modulating at least one stimulating light source which emits pulses of a stimulating color light within the selected region of the image or video at a frequency above a human's Critical Flicker Fusion (CFF) threshold of the stimulating color light;
modulating at least one compensating light source which emits pulses of a compensating color light within the selected region of the image or video, wherein the pulses of the stimulating color light have a higher amplitude and a shorter pulse duration than the pulses of the compensating color light;
embedding a combination of the pulses of stimulating color light and the pulses of compensating color light within the selected region of the retrieved image or video so that the combination of the pulses is imperceptible to a human viewer and induces a measurable response in the neural cortex of the human viewer; and
displaying the retrieved image or video with the embedded combination of pulses of stimulating color light and compensating color light.

2. The method of claim 1, wherein the image or video is a color image or video, and wherein the compensating color light and the stimulating color light have spatial luminance distributions and temporal waveforms that compensate each other so that the hue, the colorfulness, and the general display effects of the selected region of the image or video is preserved.

3. The method of claim 2, wherein an average power of the stimulating color light and an average power of the compensating color light maintain a ratio that keeps the correct balance of the hue and the colorfulness of the selected region of the color image or video.

4. The method of claim 1, wherein the stimulating light source and the compensating light source occupy the same spatial positions or form spatial patterns across a lighting surface.

5. The method of claim 1, wherein the stimulating color light and/or the compensating color light are modulated by means of frequency modulation, phase modulation, or chip sequence modulation.

6. The method of claim 1, wherein the pulses of the stimulating color light and the pulses of the compensating color light are offset or asynchronous from one another.

7. The method of claim 1, further comprising inducing and monitoring the human viewer's electroencephalographic (EEG) responses.

8. The method of claim 1, wherein the combination of the pulses of stimulating color light and the pulses of compensating color light within the selected region of the image or video is configured to prevent the pulses from causing or inducing epilepsy, migraines, or other photosensitive ailments.

9. A control system comprising a non-transitory computer readable storage medium having a computer-readable program code embodied therein, said computer-readable program code adapted to be executed to implement a method to induce measurable responses from neural cortices of a human viewer watching a displayed image or video, the control system comprising:
logic configured to retrieve an image or video from a data storage medium;
logic configured to select a region of the image or video to display a combination of colored light, wherein the selected region is less than the entire image or video;
logic configured to modulate at least one stimulating light source which emits pulses of a stimulating color light within the selected region of the image or video at a frequency above a human's Critical Flicker Fusion (CFF) threshold of the stimulating color light;
logic configured to modulate at least one compensating light source which emits pulses of a compensating color light within the selected region of the image or video, wherein the pulses of the stimulating color light have a higher amplitude and a shorter pulse duration than the pulses of the compensating color light;
logic configured to embed a combination of the pulses of stimulating color light and the pulses of compensating color light within the selected region of the retrieved image or video so that the combination of the pulses is imperceptible to a human viewer and induces a measurable response in the neural cortex of the human viewer; and logic configured to display the retrieved image or video with the embedded combination of pulses of stimulating color light and compensating color light.

10. The control system of claim 9, further comprising:

logic configured to control the spatial-temporal characteristics of the stimulating and compensating color lights as well as their timing relations;

logic configured to monitor the measurable responses of the human viewer's neural cortices through electroencephalographic (EEG) signal analysis or other indirect observation; and logic configured to provide feedback between a viewer monitoring system and a stimuli generating mechanism or device.

11. The control system of claim 10, further comprising a stimuli generating device and a brain state monitoring device, wherein the control system has an information feedback path between these two devices.

12. The control system of claim 9, further comprising a stimuli generating device, wherein the stimuli generating device comprises a light stimuli encoder that is coupled to the stimulating and compensating light sources to control the spatial-temporal characteristics of the stimulating and the compensating light, including modulation frequencies, amplitudes, relative phases, temporal waveforms, and spatial luminance distributions.

13. The control system of claim 9, further comprising a brain state monitoring device comprising:

an EEG signal amplifier that is coupled to at least one electrode and configured to amplify an EEG signal of the human viewer when the human viewer is stimulated by the imperceptible stimuli;

a signal processor that is coupled to the EEG signal amplifier to extract relevant features from the EEG signal; and a brain state analyzer that is coupled to the signal processor to receive the data of the extracted features and configured to generate analysis results of the human viewer's brain states according to the data.

14. A stimuli generating device for inducing measurable responses from neural cortices of a human viewer, the stimuli generating device comprising:

means for retrieving a color image or video from a data storage medium;

at least one stimulating light source configured to emit pulses of a stimulating color light within a selected region of the color image or video at a frequency above a human's Critical Flicker Fusion (CFF) threshold of the stimulating color light to induce a measurable response from neural cortices of the human viewer, wherein the selected region is less than the entire image or video;

at least one compensating light source configured to emit pulses of a compensating color light within the selected region of the color image or video, wherein the pulses of the stimulating color light have a higher amplitude and a shorter pulse duration than the pulses of the compensating color light so that the hue, the colorfulness, and the general display effects of the color image or video are preserved;

means for embedding a combination of emitted pulses of stimulating color light and emitted pulses of compensating color light within the selected region of the retrieved color image or video so that the combination of the pulses is imperceptible to the human viewer; and a display device for displaying the retrieved color image or video with the embedded combination of pulses of stimulating color light and compensating color light to a human viewer.

15. The device of claim 14, wherein the stimuli generating device is an image display apparatus, a lighting apparatus, or a light source indication apparatus.

16. The device of claim 15, wherein the stimuli generating device is an image display apparatus, and the display device comprises a liquid crystal display (LCD), a light emitting diode (LED) display, a cathode ray tube (CRT) display, or any display comprising pixel components configured to flicker.

* * * * *